US010744014B2

(12) United States Patent
Kumazawa et al.

(10) Patent No.: US 10,744,014 B2
(45) Date of Patent: Aug. 18, 2020

(54) STENT DELIVERY DEVICE

(71) Applicant: TERUMO KABUSHIKI KAISHA, Shibuya-ku, Tokyo (JP)

(72) Inventors: Takashi Kumazawa, Fujinomiya (JP); Kazuyoshi Tani, Kawasaki (JP)

(73) Assignee: TERUMO KABUSHIKI KAISHA, Shibuya-Ku, Tokyo (JP)

(*) Notice: Subject to any disclaimer, the term of this patent is extended or adjusted under 35 U.S.C. 154(b) by 292 days.

(21) Appl. No.: 15/682,096

(22) Filed: Aug. 21, 2017

(65) Prior Publication Data

US 2017/0340466 A1   Nov. 30, 2017

Related U.S. Application Data

(63) Continuation of application No. PCT/JP2016/052544, filed on Jan. 28, 2016.

(30) Foreign Application Priority Data

Feb. 27, 2015   (JP) .................................. 2015-039353

(51) Int. Cl.
*A61F 2/958* (2013.01)
*A61F 2/962* (2013.01)
(Continued)

(52) U.S. Cl.
CPC .............. *A61F 2/958* (2013.01); *A61F 2/962* (2013.01); *A61F 2/966* (2013.01); *A61F 2/82* (2013.01); *A61F 2002/9517* (2013.01)

(58) Field of Classification Search
CPC .......... A61F 2/958; A61F 2/962; A61F 2/966; A61F 2002/9517; A61F 2/82; A61B 17/12022; A61M 25/10; A61M 25/104
See application file for complete search history.

(56) References Cited

U.S. PATENT DOCUMENTS

| 2002/0116046 | A1 | 8/2002 | DiCaprio et al. |
| 2006/0058866 | A1* | 3/2006 | Cully ........................ A61F 2/95 623/1.11 |
| 2013/0268051 | A1 | 10/2013 | Atlani et al. |

FOREIGN PATENT DOCUMENTS

| JP | 2002-102359 A | 4/2002 |
| JP | 2014-509219 A | 4/2014 |
| WO | WO 2002/028319 A | 4/2002 |

OTHER PUBLICATIONS

The extended European Search Report dated Jul. 10, 2018, by the European Patent Office in corresponding European Patent Application No. 16755126.6-1113. (7 pages).
(Continued)

*Primary Examiner* — Elizabeth Houston
*Assistant Examiner* — Michael G Mendoza
(74) *Attorney, Agent, or Firm* — Buchanan Ingersoll & Rooney PC

(57) ABSTRACT

A stent delivery device includes a shaft with an internal lumen and a balloon connected to the shaft. The stent delivery device includes a cover configured to advance or retract in the axial direction of the shaft between a covering position where the cover covers the deflated balloon and a retracted position where the cover is spaced apart from the balloon. The stent delivery device includes a drive unit configured to apply a driving force for advancing or retracting the cover. The lumen of the shaft is configured to allow a working fluid to flow through the lumen to inflate the balloon. The balloon and drive unit are operated by the injecting and discharging of the working fluid. The inflation and deflation of the balloon and the advancing and retracting of the cover are performed in conjunction with each other.

12 Claims, 8 Drawing Sheets

(51) Int. Cl.
  *A61F 2/82* (2013.01)
  *A61F 2/95* (2013.01)
  *A61F 2/966* (2013.01)

(56) References Cited

OTHER PUBLICATIONS

International Search Report (PCT/ISA/210) dated May 24, 2016, by the Japanese Patent Office as the International Searching Authority for International Application No. PCT/JP2016/052544.
Written Opinion (PCT/ISA/237) dated May 24, 2016, by the Japanese Patent Office as the International Searching Authority for International Application No. PCT/JP2016/052544.

* cited by examiner

STENT DELIVERY DEVICE

CROSS-REFERENCES TO RELATED APPLICATIONS

This application is a continuation of International Application No. PCT/JP2016/052544 filed on Jan. 28, 2016, and claims priority to Japanese Patent Application No. 2015-039353 filed on Feb. 27, 2015, the entire content of both of which is incorporated herein by reference.

TECHNICAL FIELD

The present invention generally relates to a stent delivery device and a method involving a balloon catheter.

BACKGROUND DISCUSSION

A stenosed site or an occluded site generated in a vessel of a living body may be treated by expanding the stenosed site or the occluded site using a stent to secure the body vessel. The stent is delivered to a target site (e.g., the stenosed or occluded site), and the stent is then expanded and detained at the target site. For example, International Patent Application Publication No. 2002/028319 discusses a technique in which the stent is expanded by a balloon and is detained at the target site after the stent is delivered to the target site.

When a coat layer such as a drug layer is formed on a surface of the stent (e.g., the outer surface of the stent), the stent and the inner wall of the body vessel of the living body may interfere with each other (e.g., contact one another) while the stent is being delivered to the target site. This contact may damage the coat layer of the stent. Therefore, it is desirable to protect the stent. As an example of the stent protection means, the stent may be covered by a cover.

In this case, the stent is delivered to a target site of the living body while the stent is covered by the cover. Then, the stent is expanded along with the balloon (e.g., the balloon expands or dilates radially outward and the stent correspondingly expands or dilates radially outward so that the outer diameter of the stent increases). When the stent is expanding, the cover is moved to a position separated from the balloon and the stent (e.g., spaced apart from the balloon in the axial direction of the device) in order to prevent interference with the expanding stent. After the stent is detained (i.e., indwelled or held in position at the target site of the body lumen), the balloon is deflated, and the cover is retracted to its original position to cover the balloon (i.e., cover the outer surface of the balloon).

SUMMARY

A procedure that involves moving the cover separately from the operation for inflating or deflating the balloon may be relatively complicated, so that it may be difficult to effectively perform the procedure. If the procedure can be more effectively performed (e.g., more efficiently) while the device is inserted into a living body, the burden on a patient may be reduced, which is particularly desirable.

The stent delivery device disclosed here is capable of performing a smooth procedure when the device is inserted into a living body.

A stent delivery device includes a shaft with an internal lumen and a balloon connected the shaft. The stent delivery device includes a cover configured to advance or retract in the axial direction of the shaft between a covering position where the cover covers the deflated balloon and a retracted position where the cover is spaced apart from the balloon. The stent delivery device includes a drive unit configured to apply a driving force for advancing or retracting the cover. The lumen of the shaft is configured to allow a working fluid to flow through the lumen to inflate the balloon. The balloon and drive unit are operated by the injecting and discharging of the working fluid. The inflation and deflation of the balloon and the advancing and retracting of the cover are performed in conjunction with each other.

In the stent delivery device configured as described above, the cover is automatically moved by the drive unit while the balloon is inflated or deflated by injecting or discharging the working fluid. Therefore, separately performing an operation for inflating or deflating the balloon and performing an operation for moving the cover is unnecessary. In addition it is possible to smoothly perform a procedure when a device is inserted into a living body.

In another aspect, the disclosure involves a stent delivery device comprising: a shaft extending in an axial direction and possessing an interior, a proximal portion and a distal portion; a balloon connected to the distal portion of the shaft and expandable radially outward from a deflated condition to an inflated condition; a cover surrounding the shaft and configured to axially move between a covering position where the cover axially overlaps and covers the outer surface of the balloon in the deflated condition and a retracted position where the cover is proximal of the covering position to uncover the outer surface of the balloon and allow the balloon to be outwardly expanded; a cover moving member operatively connected to the cover to move the cover between the covering position and the retracted position; and a port. The port is configured to receive a working fluid and to first communicate with the cover moving member and to then communicate with the interior of the balloon so that the working fluid received at the port: i) is first directed to the cover moving member to operate the cover moving member and thus axially move the cover from the covering position to the retracted position; and ii) is then introduced into the interior of the balloon after the cover is axially moved toward the retracted position to outwardly expand the balloon toward the inflated condition.

This disclosure also relates to a method that includes positioning a balloon catheter at a target site in a body lumen of a living body, wherein the balloon catheter comprises a balloon and a cover that surrounds an outer surface of the balloon when the balloon catheter is positioned at the target site; injecting fluid into the balloon catheter so that the fluid axially moves the cover in a proximal direction toward a retracted position in which the outer surface of the balloon is uncovered; continuing to inject the fluid into the balloon catheter and, after the cover axially moves in the proximal direction toward the retracted position so that at least a part of the balloon is uncovered, introducing the fluid into the interior of the balloon to inflate the balloon so that the balloon outwardly expands; discharging the fluid from the interior of the balloon to deflate the balloon; and removing the balloon catheter from the target site in the body lumen of the living body.

DETAILED DESCRIPTION

Set forth below with reference to the accompanying drawings is a detailed description of embodiments of a stent delivery device and a method involving a balloon catheter representing examples of the inventive device and method disclosed here. Note that the dimensions or scales on the drawings may be exaggerated for convenience of description and illustration and are different from those of the reality.

First Embodiment

Figure 1:
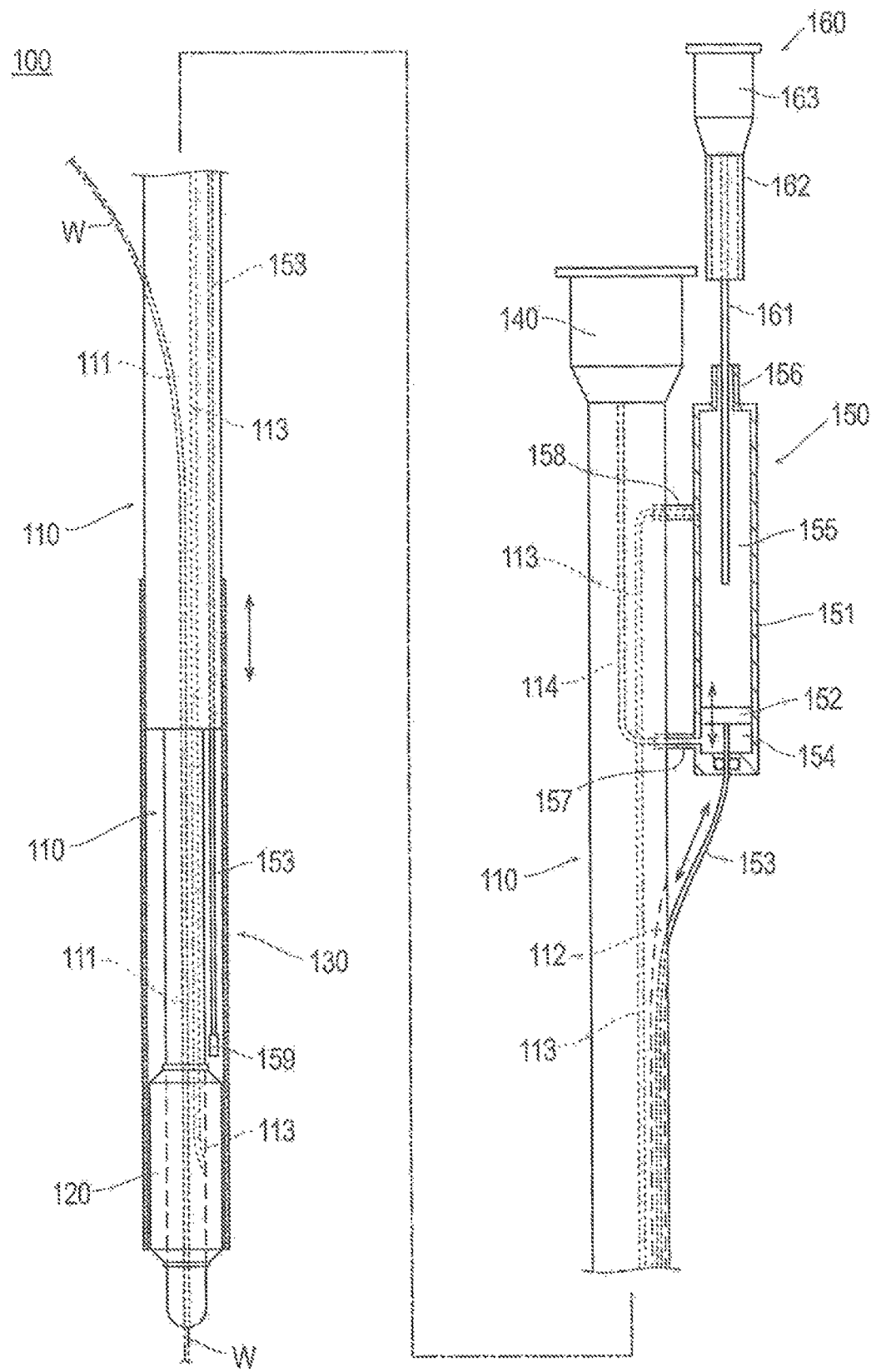
FIG. 1 is a diagram illustrating a stent delivery device according to a first embodiment.

As illustrated in FIG. 1, one embodiment of a stent delivery device 100 includes a shaft 110, a balloon 120, a sheath 130 (cover), a hub 140, a drive unit 150, and a priming device 160.

The shaft 110 includes a guidewire lumen 111, an insertion hole 112, and lumens 113 and 114. The shaft 110 is flexible. The guidewire lumen 111 and the lumens 113 and 114 are located internally within the shaft 110 as shown in FIG. 1.

A guidewire W is insertable into the guidewire lumen 111. The guidewire lumen 111 extends in an axial direction from the most distal end of the shaft 110 (i.e., distal-most end) toward the proximal end side. The proximal end of the guidewire lumen 111 is bent toward the outer circumferential surface of the shaft 110 proximal to the sheath 130 as shown in FIG. 1. The guidewire lumen 111 is not limited to such a configuration. For example, the guidewire lumen 111 may extend in the axial direction from the most distal end of the shaft 110 to the hub 140 and penetrate the shaft 110 and the hub 140 in the axial direction.

The insertion hole 112 communicates with the outside of the shaft 110 (i.e., the environment surrounding the outer surface of the shaft 110) on the outer circumferential surface of the shaft 110 distal to the drive unit 150. In addition, although not illustrated in the drawings, the insertion hole 112 extends distally in the axial direction and communicates with the sheath 130.

The lumen 113 communicates with the inside (interior) of the balloon 120. The lumen 114 communicates with the hub 140. The lumens 113 and 114 do not directly communicate with each other but communicate with one another through the drive unit 150.

The balloon 120 is provided on the distal end side of the shaft 110 and is bonded to an outer circumference of the shaft 110 (i.e., the outer surface of the shaft 110 along the outer circumference of the shaft 110) at both ends of the balloon 120 in the axial direction. The balloon 120 possesses a hollowed cylindrical shape and can be inflated or deflated around the axial direction of the shaft 110. In other words, the balloon 120 is inflatable or deflatable between an inflated state and a deflated state.

The balloon 120 may be formed of a material having a relatively high elastic property (i.e., a relatively elastic material) and may be inflated such that the material expands radially outward as the internal pressure in the interior of the balloon 120 increases. Alternatively, the balloon 120 may be formed of a material having a relatively low elastic property (i.e., a relatively less elastic material or a relatively rigid material) so that the balloon 120 can be folded around the shaft 110 in the deflated state and can be unfolded and inflated as the internal pressure in the interior of the balloon 120 increases. The balloon 120 may be formed of a material similar to that of balloon materials well known in the art that are used to expand a stent.

Figure 3:
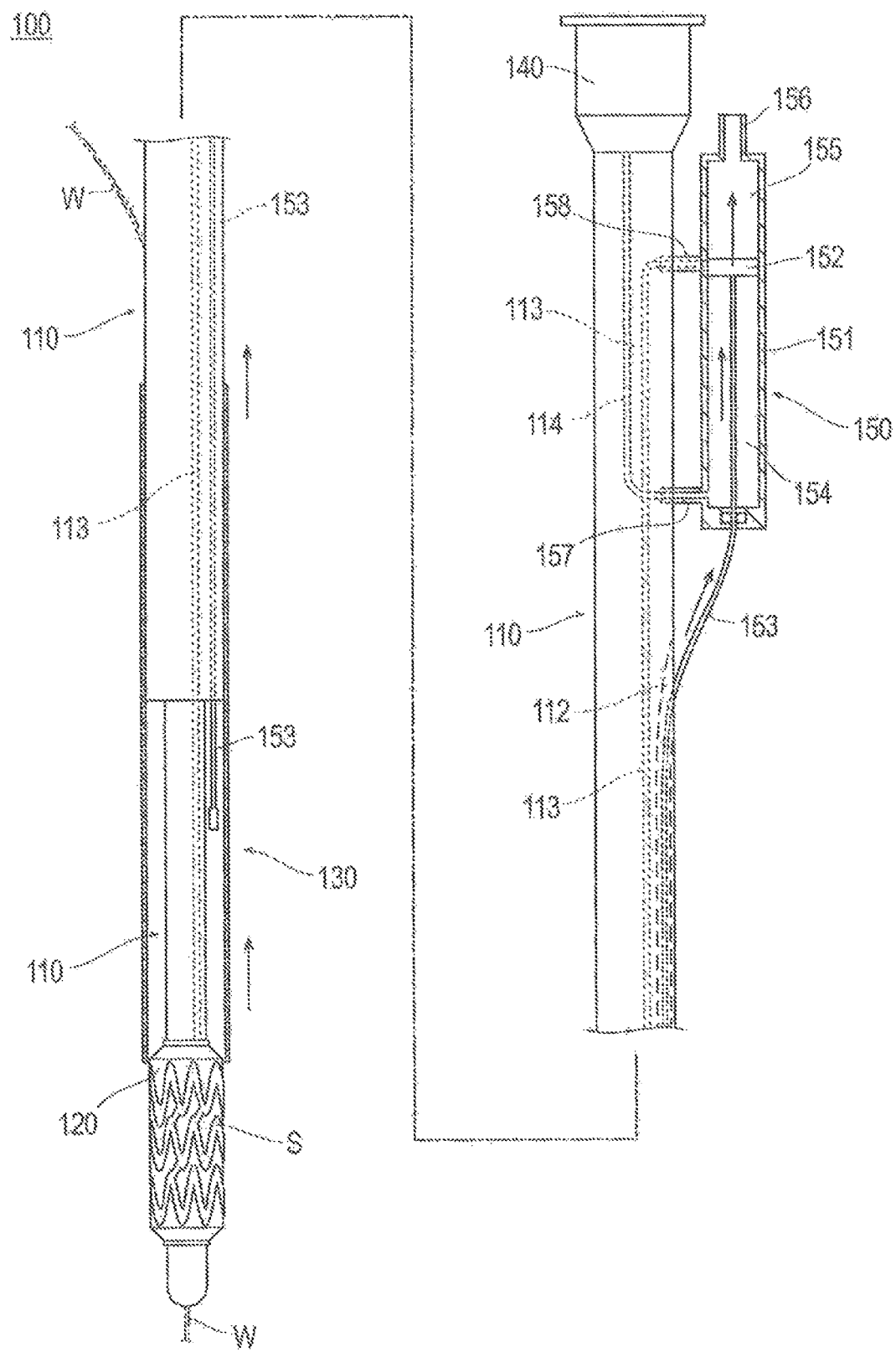
FIG. 3 is a diagram illustrating the stent delivery device according to the first embodiment when a sheath is moved to a retracted position to be spaced apart from the balloon.

The sheath 130 is configured to freely advance and retract between a covering position in which the sheath 130 covers (i.e., axially overlaps to surround) the deflated balloon 120 as illustrated in FIG. 1 and a retracted position in which the sheath 130 deviates from the covering position proximally in the axial direction and is separated from the balloon 120. In other words, the sheath 130 in the retracted position is moved proximally relative to the balloon 120 to be spaced apart from the balloon 120 in the axial direction to uncover the outer surface of the balloon 120 (i.e., expose the outer surface of the balloon 120 to the environment) as shown in FIG. 3.

The outer surface of the sheath 130 is preferably formed of a material having a low frictional resistance (i.e., relatively low resistance to friction or relatively able to be maneuvered with minimal friction). The sheath 130 can smoothly advance or retract relative to the balloon 120 by using a material possessing relatively low resistance to friction, and friction between the outer surface of the balloon 120 and the inner surface of the sheath 130 can be suppressed. The inner surface of the sheath 130 material, for example, may be polytetrafluoroethylene (PTFE). The sheath 130 may be radiopaque.

The hub 140 (a port) is provided in the proximal end of the shaft 110 and is connected to a supply/discharge device such as an indeflator (not illustrated) that supplies or discharges the working fluid. The working fluid includes, for example, a contrast medium or a mixture of a contrast medium and saline, but the working fluid is not limited to these fluids.

The drive unit 150 has a cylinder 151 (housing portion) and a piston 152 (a cover moving member) within the cylinder 151. The drive unit 150 also includes a wire 153 that acts as a driving force transmission portion to transmit a force to the sheath 130 (i.e., to transmit a force from the piston 152 to the sheath 130).

The piston 152 is slidably housed in the cylinder 151 and is slidable along the axial direction relative to the cylinder 151. The cylinder 151 is formed such that a motion and/or position of the piston 152 in the axial direction can be visually recognized from the outside of the cylinder 151. The inside of the cylinder 151 is divided by the piston 152 into a first chamber 154 and a second chamber 155 (i.e., the first chamber 154 is on one side of the piston 152 and the second chamber 155 is on the other side of the piston 152 in the axial direction) as shown in FIG. 1.

The cylinder 151 has a ventilation hole 156 that allows the second chamber 155 to communicate with the outside environment. The ventilation hole 156 is provided in the proximal end of the cylinder 151. As the piston 152 slides in the axial direction within the cylinder 151, external air flows into the second chamber 155 through the ventilation hole 156 or air within the second chamber 155 is discharged to the outside environment from the second chamber 155.

The cylinder 151 has a first communication portion 157 (an inlet port) that communicates with the first chamber 154. The cylinder 151 has a second communication portion 158 (an outlet port) that communicates with the second chamber 155. Each of the first and second communication portions 157 and 158 protrudes perpendicularly to the axial direction.

Fitting holes that allow insertion and removal of each of the first and second communication portions 157 and 158 are provided on the outer circumferential surface of the proximal end side of the shaft 110. By inserting the first and second communication portions 157 and 158 into the fitting holes, the drive unit 150 can be detachably attached to the shaft 110 (i.e., the drive unit 150 may be removed by removing the first and second communication portions 157 and 158 from the fitting holes).

When the drive unit 150 is attached to shaft 110, the first communication portion 157 communicates with the lumen 114, and the second communication portion 158 communicates with the lumen 113. As a result, the working fluid is injected into or discharged from the drive unit 150, so that the drive unit 150 has an operable state. That is, the working fluid may be injected into the lumen 114, flow through the first communication portion 157, flow into the interior of the cylinder 151, flow through the second communication portion 158 and flow into the lumen 113 to flow into the interior of the balloon 120 to inflate the balloon 120. When the drive unit 150 is removed from the shaft 110, the working fluid is not injected into or discharged from the drive unit 150. Therefore, the drive unit 150 has an inoperable state.

The wire 153 connects the piston 152 and the sheath 130. The wire 153 is slidably extracted from the cylinder 151. The wire 153 extends to the inside (interior) of the sheath 130 through the insertion hole 112. The wire 153 is bonded to the inner circumferential surface of the sheath 130 at a bonding portion 159 provided at the distal end of the wire 153 as shown in FIG. 1.

The wire 153 material may be, for example, metal or resin. The wire preferably has a certain degree of stiffness in order to transmit an axial force applied to the piston 152 to the sheath 130, but the degree of stiffness of the wire is not particularly limited.

The priming device 160 includes a piston rod 161, a priming tube 162, and a hub 163.

The piston rod 161 is a bar-like member that protrudes from an opening of the distal end of the priming tube 162. The piston rod 161 is insertable into the inside of the cylinder 151 from (i.e., via) the ventilation hole 156.

The priming tube 162 is detachably attached to the ventilation hole 156. When the priming tube 162 is connected to the ventilation hole 156, the priming tube 162 communicates with the second chamber 155.

The hub 163 possesses a hollow shape and communicates with the priming tube 162. The proximal end of the hub 163 is connected to a supply/discharge device such as a syringe (not illustrated) that supplies or discharges a priming liquid. The priming liquid includes, for example, saline, a contrast medium, or a mixture of saline and a contrast medium.

Next, the operation of the stent delivery device 100 will be described.

Figure 2:
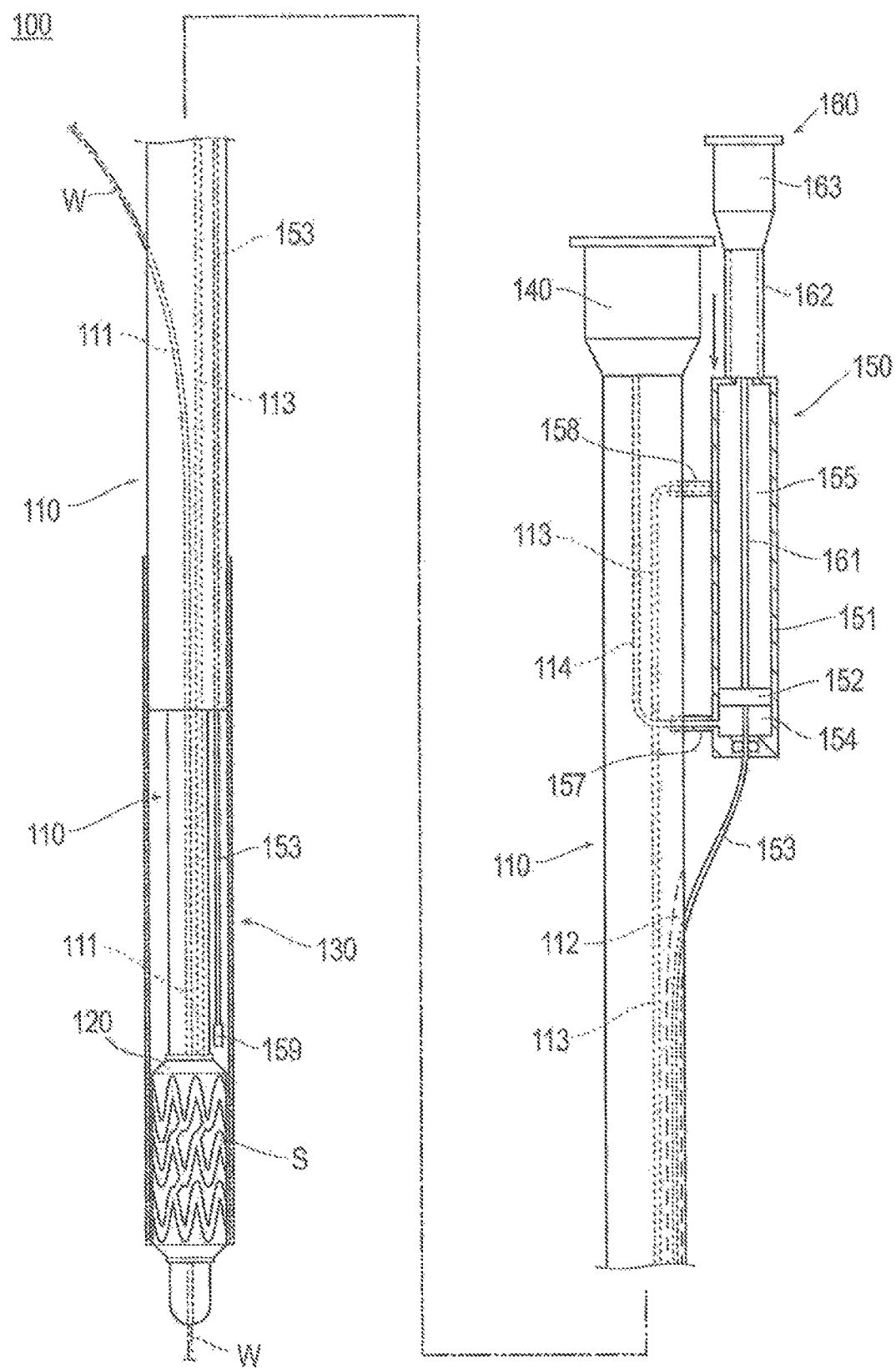
FIG. 2 is a diagram illustrating the stent delivery device according to the first embodiment with a stent attached to the stent delivery device.

As illustrated in FIG. 2, the stent delivery device 100 delivers the stent S to a lesion such as a stenosed site or an occluded site (i.e., a target site) generated in a vessel of a living body while the stent S attached to the outer circumference of the deflated balloon 120 is covered by the sheath 130. The distal end side of the stent delivery device 100 is inserted into a body vessel, and the hub 140, the drive unit 150, and the priming device 160 are used (i.e., operated by a user or operator) outside the living body. The vessels to which the stent delivery device 100 is applied may include, for example, a blood vessel, a bile duct, an esophagus, a trachea, a urethra, or the like, but the vessels are not limited to any specific body vessels.

The stent S may possess a mesh tubular shape, but the shape and material of the stent S are not particularly limited. The stent S is formed of, for example, metal or resin. Alternatively, a part of the stent S may be formed of resin, and the other parts may be formed of metal. The stent S may have biodegradability (i.e., the stent S may be biodegradable or degradable within a living body). In addition, the stent S may have a coat layer such as a drug layer on the outer surface of the stent S.

The stent delivery device 100 can be delivered to a target lesion along the guidewire W introduced into a vessel in advance. As the guidewire W is inserted into the guidewire lumen 111, the distal end side of the stent delivery device 100 is moved along the guidewire W without being apart from the guidewire W. After the distal end side of the stent delivery device 100 reaches a target lesion, the stent S is deployed so that the stent S is detained (i.e., held in position) at the target site.

Prior to detaining of the stent S, priming is performed such that the air in the balloon 120, the shaft 110, and the cylinder 151 is discharged by filling the balloon 120, the shaft 110, and the cylinder 151 with priming liquid.

The priming device 160 is attached to the cylinder 151 when priming the stent delivery device 100. In this case, the piston rod 161 abuts on (i.e., directly contacts) the piston 152, and the priming tube 162 communicates with the cylinder 151. In this state, the supply/discharge device (not illustrated) is connected to the proximal end of the hub 163.

As the supply/discharge device connected to the hub 163 suctions air, the suctioned air is discharged from the balloon 120, the lumen 113, and the second chamber 155 through the priming tube 162 and the hub 163. The piston 152 abuts on the piston rod 161 when the air is being suctioned, so that the piston 152 is restricted from sliding toward the proximal end side. The piston rod 161 restricts the piston 152 from moving proximally beyond the second communication portion 158, so that the piston 152 does not hinder the air from being discharged from the lumen 113 and the balloon 120 through the second communication portion 158.

The supply/discharge device connected to the hub 163 supplies the priming liquid after the air is discharged. The priming liquid flows from the priming tube 162 into the second chamber 155 and fills the lumen 113 and the balloon 120 through the second communication portion 158.

By filling (injecting or introducing) the priming liquid into the lumen 113 and the balloon 120, it is possible to make it easy to apply a pressure to the inside of the balloon 120 to inflate the balloon 120. In addition, it is possible to reduce a possibility that the air contained in the stent delivery device 100 is input to the living body because the air is discharged by performing priming.

After the priming, the priming device 160 is removed from the cylinder 151 to extract the piston rod 161. As a result, the piston rod 161 is separated from the piston 152, and the restriction of the movement of the piston 152 is released. Therefore, the piston 152 can freely slide within the cylinder 151. The stent S is next deployed in the body vessel.

Figure 4:
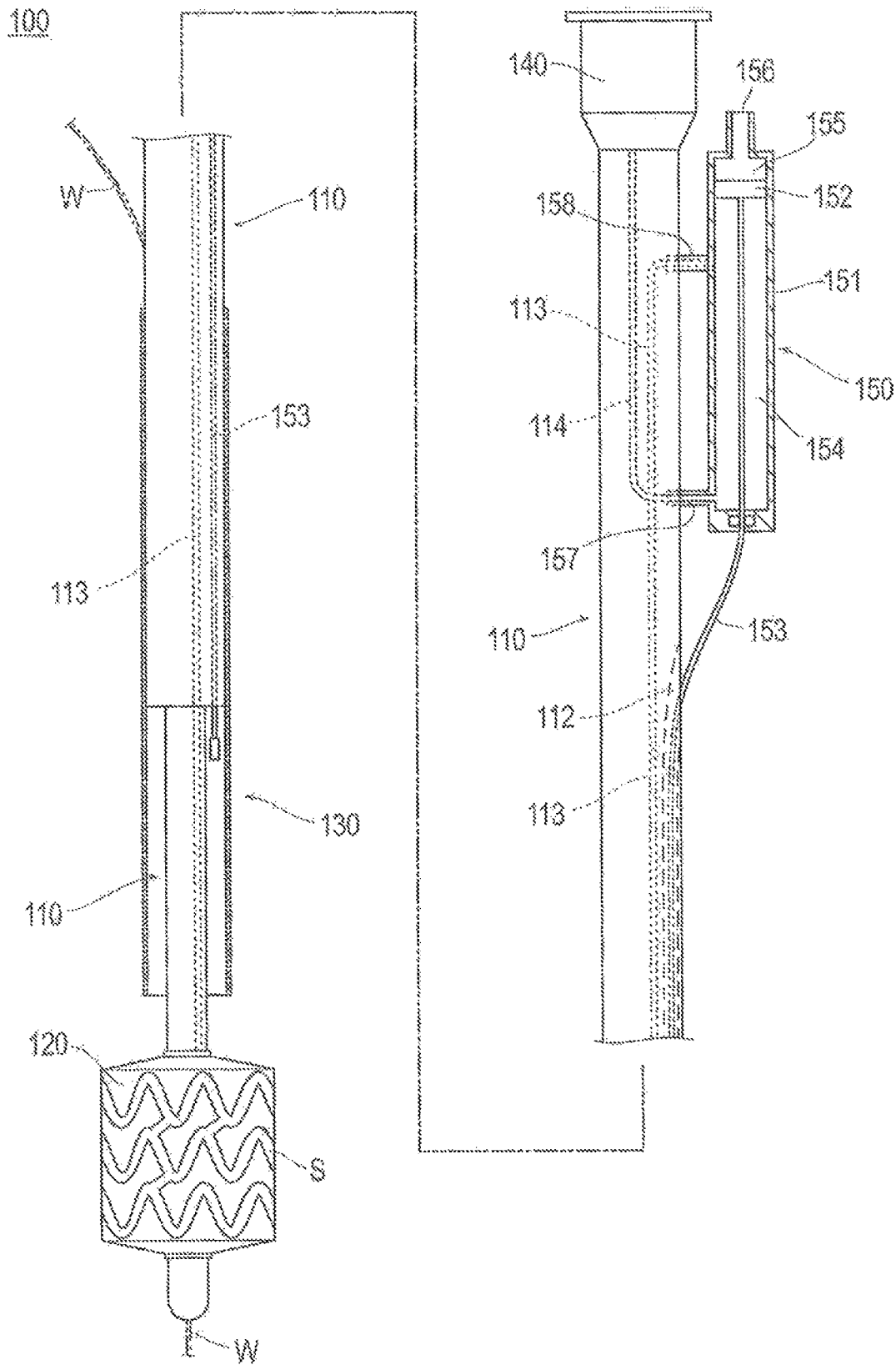
FIG. 4 is a diagram illustrating the stent delivery device according to the first embodiment when the balloon is inflated to expand the stent radially outwardly.

In order to deploy the stent S, the drive unit 150 moves the sheath 130 toward the proximal end side in the axial direction (i.e., proximally) so that the sheath 130 is spaced apart from the balloon 120 and the stent S in the axial direction as illustrated in FIG. 3 (e.g., by a predetermined distance). The balloon 120 then inflates to deploy the stent S by expanding the stent S radially outward as illustrated in FIG. 4. The drive unit 150 and the balloon 120 are operated by introducing the working fluid into the shaft 110.

Prior to the start of inflation of the balloon 120, the drive unit 150 retracts the sheath 130 to a retracted position spaced apart from the balloon 120 and the stent S in the axial direction (i.e., proximal to the balloon 120 and the stent S to uncover the balloon 120 and the stent S). Then, the balloon 120 is inflated together with the stent S (i.e., the inflation of the balloon 120 causes the stent S on the outer surface of the balloon 120 to expand radially outwardly). Introducing the working fluid into the shaft 110 thus causes the sheath 130 to move and the balloon 120 to inflate in conjunction with one another.

The working fluid is supplied from a supply/discharge device connected to the hub 140 and is introduced into the first chamber 154 through the lumen 114 and the first communication portion 157 (i.e., the inlet port of the cylinder 151). As the working fluid is introduced into the first chamber 154, the piston 152 receives a force urging the piston 152 proximally in the axial direction. This force (driving force) is transmitted to the sheath 130 through the wire 153. As a result, the sheath 130 is moved toward the proximal end side (i.e., proximally) in the axial direction.

While the piston 152 is distal to the second communication portion 158, the first chamber 154 does not communicate with the second communication portion 158 and the lumen 113 as illustrated in FIG. 3. The working fluid is thus not supplied to the balloon 120. Therefore, the balloon 120 is not inflated. Meanwhile, the sheath 130 is pulled (i.e., retracted) toward the proximal end side (i.e., proximally) in the axial direction along with the proximal movement of the piston 152. The sheath 130 is thus moved to the retracted position, which is spaced apart from the balloon 120 in the axial direction. When the sheath 130 is moved to the retracted position, both the balloon 120 and the stent S are exposed to the outside of the sheath 130 (i.e., the balloon 120 and the stent S are uncovered).

As the piston 152 is moved proximally beyond the second communication portion 158, the first chamber 154 communicates with the second communication portion 158 and the lumen 113 as illustrated in FIG. 4. Therefore, the working fluid is supplied to the balloon 120 to inflate the balloon 120. The sheath 130 does not hinder inflation of the balloon 120 and expansion of the stent S because the sheath 130 is in the retracted position.

The stenosed site or the occluded site in the vessel is inflated (i.e., the inner diameter of the stenosed or occluded site is expanded) as the balloon 120 is inflated. Then, the stent delivery device 100 deploys the stent S to indwell the body lumen and the stent delivery device 100 is removed from the vessel.

Figure 5:
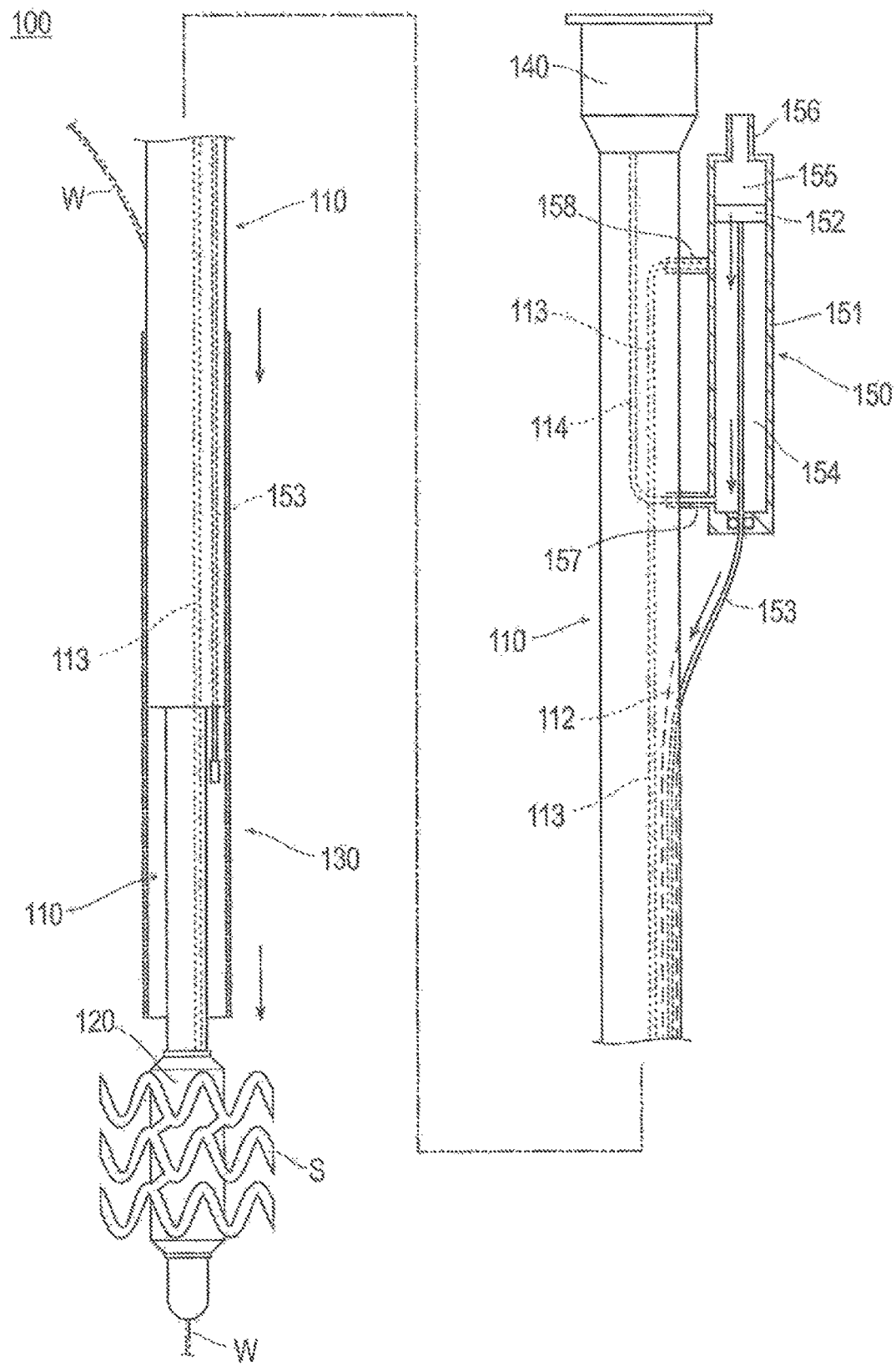
FIG. 5 is a diagram illustrating the stent delivery device according to the first embodiment when the sheath is moved to cover the balloon.

In this case, as illustrated in FIG. 5, the stent delivery device 100 deflates the balloon 120, and then the sheath 130 moves distally to cover the deflated balloon 120. The expanded stent S is maintained in the expansion state even when the balloon 120 is deflated. The stent S is detained (i.e., indwelled or held in place) in the vessel inside the living body in the expanded state to hold the stenosed site or the occluded site of the vessel in the expansion state.

The balloon 120 is deflated by discharging the working fluid through the lumen 113. The working fluid discharged from the balloon 120 is suctioned by the supply/discharge device connected to the hub 140 through the lumen 113, the second communication portion 158, the first chamber 154, the first communication portion 157, and the lumen 114.

This suctioning causes the working fluid to be discharged from the first chamber 154 through the first communication portion 157. As a result of the discharge of the working fluid from the first chamber 154, the piston 152 moves distally in the axial direction, and the drive unit 150 transmits a force (driving force) to urge the piston 152 distally in the axial direction. The driving force applied to the piston 152 is transmitted (i.e., applied) to the sheath 130 through the wire 153. For this reason, the sheath 130 moves distally to the covering position in conjunction with the deflation of the balloon 120.

Here, the deflation of the balloon 120 begins before the piston 152 and the sheath 130 move because the balloon 120 is relatively easily deflated after the stent S is removed. Therefore, the sheath 130 begins to move after the balloon 120 is deflated (i.e., the sheath 130 is configured to cover the balloon 120 after the balloon 120 deflates).

The sheath 130 is moved to the covering position in which the sheath 130 covers (i.e., surrounds the outer surface) the entire deflated balloon 120 (refer to FIG. 1). Then, the stent delivery device 100 is removed from the vessel.

Next, functional effects of this embodiment will be described.

In a case where, for example, an operator moves the sheath 130 by manually pulling the wire 153, the sheath 130 is moved to the retreated portion before the working fluid is introduced into the shaft 110 to inflate the balloon 120. Therefore, the operator is required to separately perform an operation for manually pulling the wire 153.

Additionally, when the deflated balloon 120 needs to be covered by the sheath 130 again, an operator is required to move the sheath 130 to the covering position by manually pushing the wire 153 distally after the operation of deflating the balloon 120 by suctioning the working fluid from the balloon 120.

In contrast, in the stent delivery device 100 as described above and illustrated in FIGS. 1-5, the sheath 130 is automatically moved by the drive unit 150 as the balloon 120 is inflated or deflated by injecting or discharging the working fluid to or from the shaft 110. For this reason, it is not necessary to perform a separate operation for inflating and deflating the balloon 120 and moving the sheath 130 (unlike the aforementioned example). Therefore, the balloon 120 can be effectively inflated and deflated and the sheath 130 can be moved to smoothly and efficiently perform a procedure while the stent delivery device 100 is inserted into the vessel of a living body.

The cylinder 151 is transparent so that the piston 152 is visual from the outside. For this reason, an operator can easily and simply predict a position or motion of the sheath 130 (which is moved along with the piston 152) by visually checking a position or motion of the piston 152 even when the distal end side of the stent delivery device 100 is inserted into the living body. In addition, an operator can accurately adjust a position or motion of the sheath 130 on the basis of this visual check.

The piston 152 abuts on the piston rod 161 for priming so that the movement of the piston 152 is restricted. The sheath 130 connected to the piston 152 thus does not move, and so the sheath 130 can be prevented from unintentionally moving during the priming. More specifically, when air in the second chamber 155 is suctioned by the priming, the piston rod 161 abuts on the piston 152, and the proximal movement of the piston 152 is restricted. Therefore, it is possible to prevent the sheath 130 from being unintentionally moved to the retracted position during the priming.

The drive unit 150 moves the sheath 130 to the retracted position before a start of the inflation of the balloon 120 (i.e., before the balloon 120 begins to be inflated). For this reason, the movement of the sheath 130 toward the retracted position is not interrupted by the inflation of the balloon 120. In addition, the inflation of the balloon 120 is not prevented by the sheath 130 (i.e., the sheath 130 moves to uncover the balloon 120). Therefore, it is possible to reliably move the sheath 130 toward the retracted position and inflate the balloon 120.

The drive unit 150 moves the sheath 130 to the covering position after the deflation of the balloon 120 begins. When the sheath 130 reaches the covering position, the balloon 120 is thus already deflated (i.e., in a deflated state). Therefore, the sheath 130 and the balloon 120 do not easily interfere with each other (i.e., contact one another), and the balloon 120 can be easily fitted into the sheath 130 (i.e., so that the sheath 130 covers or surrounds the balloon 120).

The drive unit 150 is not operated while the drive unit 150 is removed from the shaft 110. Therefore, by removing the drive unit 150 from the shaft 110, it is possible to prevent the sheath 130 from unintentionally advancing or retracting. This prevents the balloon 120 from being unintentionally inflated or deflated. Accordingly, it is possible to prevent an erroneous operation.

Second Embodiment

Figure 6:
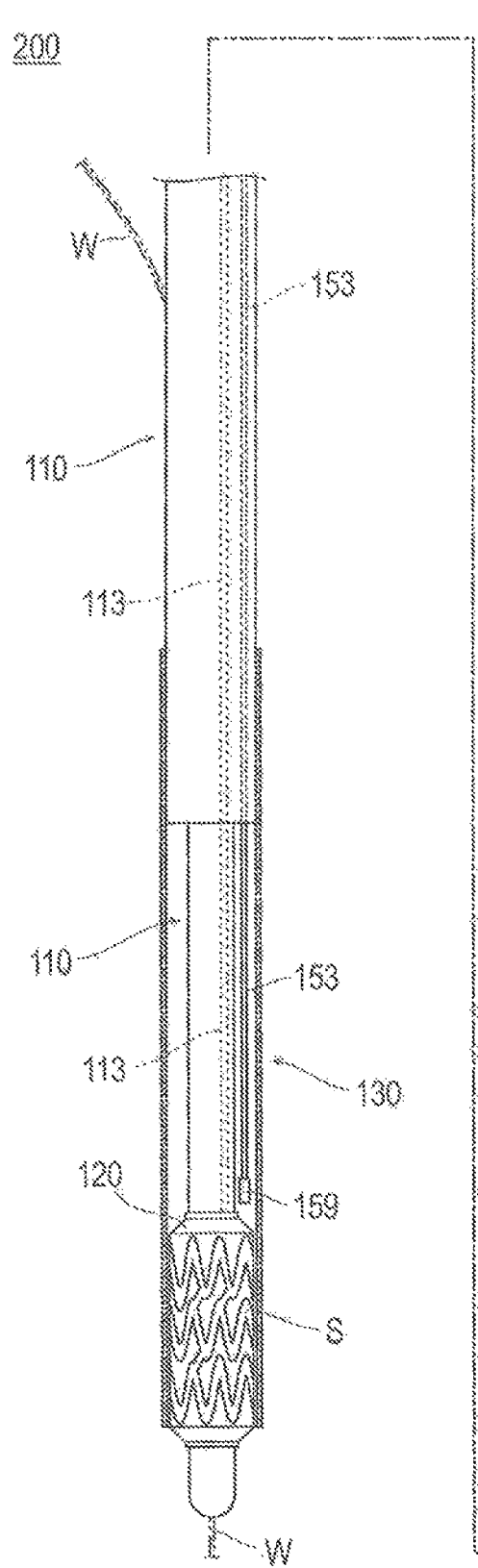
FIG. 6 is a diagram illustrating a stent delivery device according to a second embodiment.
Figure 6:
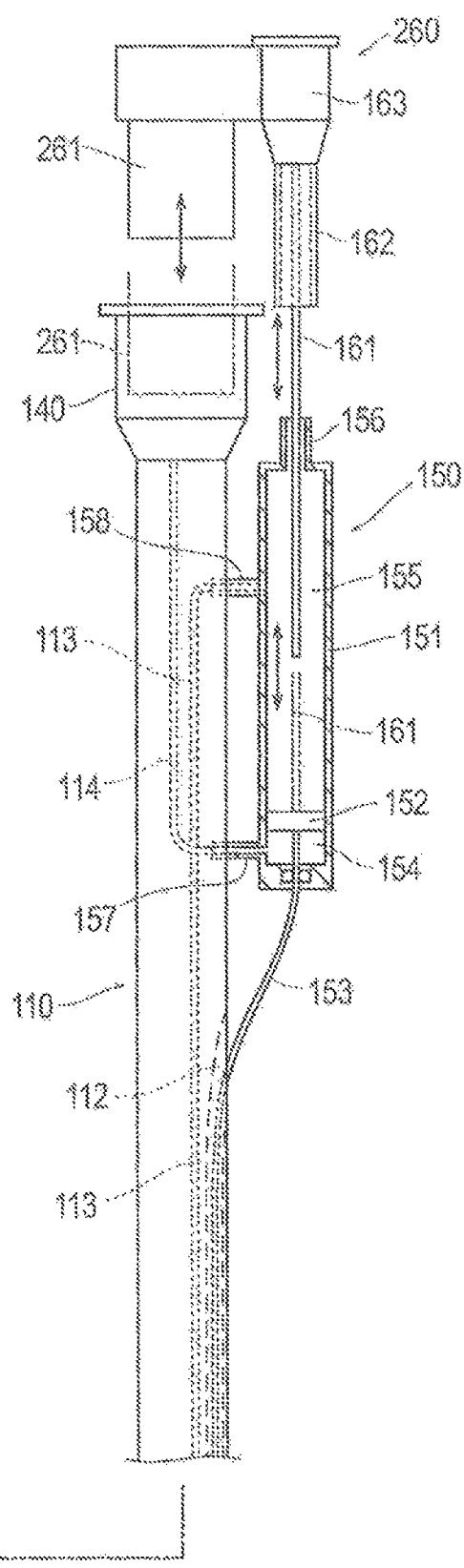

A stent delivery device 200 according to another embodiment illustrated in FIG. 6 includes a priming device 260 that is different from that the priming device 160 of the first embodiment. Other configurations of the stent delivery device 200 are similar to those of the stent delivery device 100 of the first embodiment, and a description of the similar aspects will not be repeated.

The priming device 260 includes a piston rod 161, a priming tube 162, a hub 163, and a hub 261 (plug member). The hub 261 is formed integrally with the piston rod 161, the priming tube 162, and the hub 163. The piston rod 161, the priming tube 162, and the hub 163 are similar to those of the first embodiment.

As the piston rod 161 is inserted into the cylinder 151, the hub 261 is inserted into the hub 140 to block (i.e., plug) the hub 140. As a result, the priming liquid is not erroneously injected into the hub 140 (i.e., the priming liquid is prevented from being erroneously injected into the hub 140). Therefore, it is possible to prevent an erroneous operation of the piston 152 and to prevent the sheath 130 from being unintentionally moved during the priming. More specifically, since the priming liquid is not erroneously injected into the first chamber 154 through the hub 140 and the lumen 114, it is possible to prevent the sheath 130 from being unintentionally moved to the retracted position during the priming.

The hub 140 is also reliably blocked as the piston rod 161 is inserted into the cylinder 151 since the hub 261 is integrally assembled with the piston rod 161. Therefore, it is possible to prevent an operator from forgetting to block the hub 140.

Other functional effects according to this embodiment caused by components common to the first embodiment are similar to those of the first embodiment.

After the priming, the hub 261 is extracted along with the piston rod 161 and is removed from the hub 140.

Third Embodiment

Figure 7:
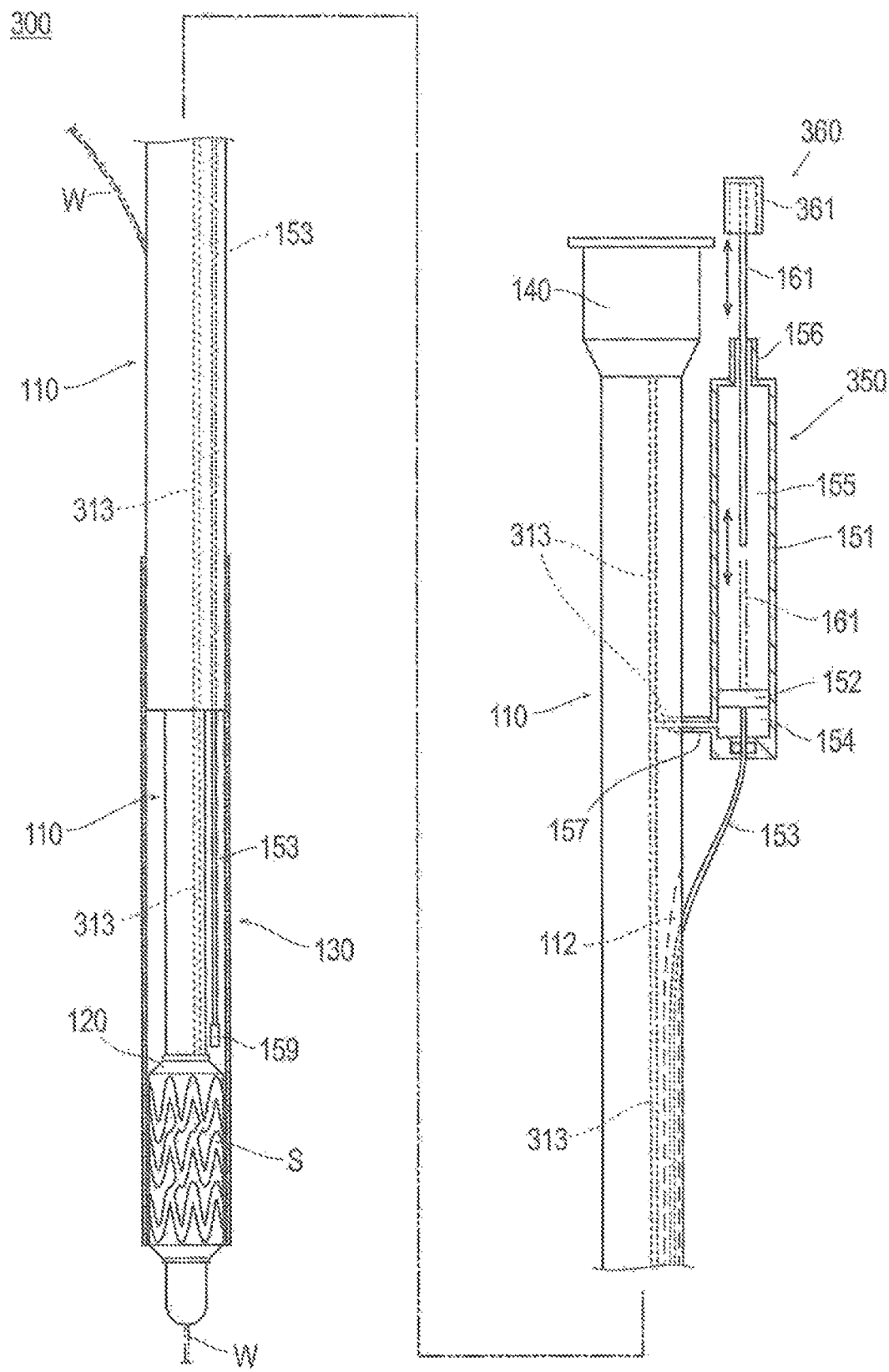
FIG. 7 is a diagram illustrating a stent delivery device according to a third embodiment.

A stent delivery device 300 according to yet another embodiment illustrated in FIG. 7 includes a drive unit 350, a lumen 313, and a priming device 360 different from those described above. Other configurations of the stent delivery device 300 are similar to those described above, and a description of the similar aspects will not be repeated.

The lumen 313 communicates with the balloon 120 in the distal end side. The lumen 313 is branched in the proximal end side so as to communicate with the drive unit 350 and the hub 140. The drive unit 350 according to the third embodiment is different from the drive unit 150 of the first embodiment because the second communication portion 158 is removed.

The priming device 360 has a piston rod 161 and a hub 361. The piston rod 161 is similar to that of the first embodiment. The hub 361 is detachably attached to the ventilation hole 156.

For the priming, the hub 361 is connected to the ventilation hole 156 to block the ventilation hole 156. In this case, the piston rod 161 abuts on the piston 152 to restrict the piston 152 from sliding toward the proximal end side. According to this embodiment, the priming is performed using a supply/discharge device (not illustrated) connected to the hub 140.

As the supply/discharge device connected to the hub 140 suctions air, the air from the lumen 313 and the balloon 120 is discharged. The air does not flow to the cylinder 151 because the hub 361 blocks the ventilation hole 156.

The supply/discharge device connected to the hub 140 supplies the priming liquid after the air is discharged. The priming liquid fills the lumen 313 and the balloon 120 through the hub 140. In this case, it is possible to prevent an unintentional movement of the sheath 130 connected to the piston 152 because the piston rod 161 abuts the piston 152 to restrict the piston 152 from sliding proximally.

After the priming, the priming device 360 is removed from the cylinder 151 by extracting the piston rod 161, and the piston rod 161 is separated from the piston 152. As a result, the restriction of the movement of the piston 152 is released, and the piston 152 can freely slide inside the cylinder 151.

Then, the working fluid is supplied from the supply/discharge device connected to the hub 140 to the shaft 110 to move the sheath 130 and inflate the balloon 120 and the stent S.

The working fluid flows to the first chamber 154 through the lumen 313 and the communication portion 157. As a result, the piston 152 moves proximally in the axial direction, and the sheath 130 is pulled toward the proximal end side (i.e., proximally) in the axial direction using the wire 153 and is moved to the retracted position.

In this case, the working fluid also flows to the balloon 120 through the lumen 313. However, since an inflation pressure P2 necessary to inflate the balloon 120 attached with the stent S is higher than a pressure P1 necessary to slide the piston 152 (P2>P1), the balloon 120 is either not inflated or is very slightly inflated.

The pressure P1 necessary to slide the piston 152 is, for example, 1.5 to 2 atm. The inflation pressure P2 for the balloon 120 (i.e., the pressure necessary to inflate the balloon 120) attached with the stent S is, for example, 3 to 4 atm.

After the sheath 130 is moved to the retracted position, an operator increases the pressure of the working fluid supplied to the shaft 110. When the pressure is equal to or higher than the inflation pressure P2, the balloon 120 inflates to expand the stent S radially outwardly.

After the stent S is deployed, the working fluid is discharged by using the supply/discharge device connected to the hub 140 through the lumen 313.

An absolute value P3 of the negative pressure necessary to deflate the balloon 120 after removing the stent S is smaller than the absolute value P1 of the negative pressure necessary to slide the piston 152 (P1>P3). For this reason, as the supply/discharge device connected to the hub 140 suctions the working fluid, the balloon 120 is deflated before the piston 152 starts to be moved. Then, when the balloon 120 is further depressurized, the piston 152 moves distally in the axial direction. The sheath 130 thus moves to the covering position to cover the deflated balloon 120.

Since the stent delivery device 300 has the same function as that of the first embodiment, the same effects as those of the first embodiment can be obtained from the third embodiment. Note that, according to the third embodiment, the piston rod 161 may not be necessary by optimizing a sliding resistance so as not to excessively lower friction between the piston 152 and the cylinder 151. As a result, it may be possible to reduce cumbersomeness (i.e., complexity) or cost by simplifying the entire system as done in the third embodiment.

The present invention is not limited to the aforementioned embodiments, and various modifications may be possible without departing from the scope of the claims.

For example, the drive unit 150 may be fixed (i.e., permanently fixed) to the shaft 110 instead of being detachably attached. In addition, the housing portion 151 that houses the piston 152 so that the piston 152 is slidable may be provided in the shaft 110 itself.

In the drive units 150 and 350, it is also not necessary to form the entire cylinder 151 with a transparent material. A window through with the piston 152 is visible may be provided in only a part of the cylinder 151.

The drive units 150 and 350 begin the movement of the sheath 130 at a time that is deviated from the inflation/deflation timing of the balloon 120. However, the sheath 130 movement is not limited thereto. The inflation/deflation of the balloon 120 and the movement of the sheath 130 may begin simultaneously. For example, even when the deflation of the balloon 120 and the movement of the sheath 130 to the covering position begin simultaneously, the sheath 130 and the balloon 120 do not interfere with each other. The balloon 120 can thus be easily inserted into the sheath 130 if the balloon 120 is deflated when the sheath 130 reaches the balloon 120.

Figure 8:
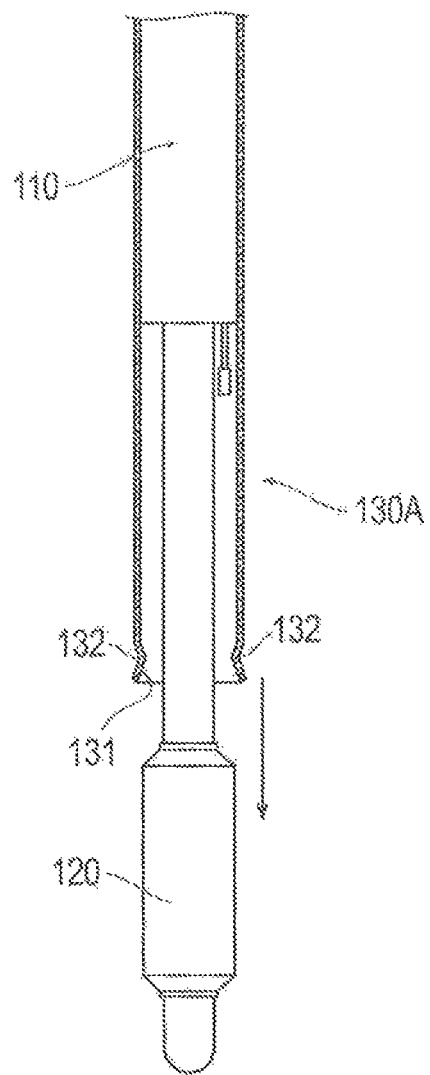
FIG. 8 is a diagram illustrating a modification of the sheath.

In addition, the cover is not limited to the sheath 130 described above. The cover may include, for example, a sheath 130A illustrated in FIG. 8.

The sheath 130A is shaped to have a tapered portion 131 at the distal end of the sheath 130A in the retracted position. The tapered portion 131 opens to be widened toward the distal end side (i.e., widens at the distal end) in the axial direction. A protrusion 132 protruding inward in the radial direction (i.e., radially inward) is formed in the proximal end of the tapered portion 131.

The sheath 130A is formed of a flexible material. Therefore, when the sheath 130A moves to the covering position to cover the balloon 120, the protrusion 132 deforms to follow the shape of the balloon 120 and has a tubular shape such as the sheath 130 of FIG. 1.

Since the sheath 130A has the tapered portion 131 in the distal end in the retreated position, the balloon 120 is smoothly guided to the sheath 130A using the tapered portion 131 when the sheath 130A is moved to the covering position to cover the balloon 120. Therefore, it is possible to easily insert the balloon 120 into the sheath 130A.

The detailed description above describes a stent delivery system and a method involving a balloon catheter. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A stent delivery device comprising:
   a shaft comprising an internal lumen, the shaft extending in an axial direction;
   a balloon connected the shaft, the balloon being inflatable radially outward and deflatable radially inward between a deflated state and an inflated state;
   a cover configured to advance or retract in the axial direction of the shaft between a covering position where the cover covers the balloon when the balloon is in the deflated state and a retracted position where the cover is axially spaced apart from the balloon;
   a drive unit configured to apply a driving force for advancing or retracting the cover in the axial direction;
   the lumen of the shaft being configured to allow a working fluid injected into the lumen of the shaft to flow into the balloon to inflate the balloon, the working fluid being dischargeable from the lumen of the shaft, the balloon and drive unit being operated by the injecting and discharging of the working fluid; and
   the inflating and deflating of the balloon and the advancing and retracting of the cover being performed in conjunction with each other, wherein
   the drive unit has a piston connected to the cover and a housing portion configured to house the piston so that the piston is slidable within the housing portion relative to the housing portion, and
   the drive unit comprises a piston rod that extends into the housing portion, the piston rod being moveable to abut the piston to restrict the piston from sliding within the housing portion and retractable from the piston to release the sliding restriction on the piston.

2. The stent delivery device according to claim 1, wherein at least a part of the housing portion is formed so that the piston is visual.

3. The stent delivery device according to claim 1, wherein the drive unit is configured to perform at least one of moving the cover toward the retracted position before starting the inflation of the balloon and moving the cover toward the covering position after starting the deflation of the balloon.

4. The stent delivery device according to claim 1, wherein the drive unit is detachably attached to the shaft,
   the drive unit is not operable to apply the driving force when the drive unit is detached from the shaft, and
   the drive unit is operable to apply the driving force when the drive unit is attached to the shaft.

5. The stent delivery device according to claim 1, wherein a distal end portion of the cover is shaped to have a tapered portion opened to be widened toward a distal end side of the axial direction in the retracted position.

6. The stent delivery device according to claim 1, wherein
a stent is attached to an outer circumference of the balloon, and
the stent is covered by the cover when the cover is in the covering position.

7. A stent delivery device comprising:
a shaft extending in an axial direction, the shaft possessing an interior, a proximal portion and a distal portion;
a balloon connected to the distal portion of the shaft, the balloon being expandable radially outward from a deflated condition to an inflated condition, the balloon possessing an outer surface and an interior;
a cover surrounding the shaft, the cover being configured to axially move between a covering position where the cover axially overlaps and covers the outer surface of the balloon in the deflated condition and a retracted position where the cover is proximal of the covering position to uncover the outer surface of the balloon and allow the balloon to be outwardly expanded;
a cover moving member operatively connected to the cover to move the cover between the covering position and the retracted position; and
a port configured to receive a working fluid and to first communicate with the cover moving member and to then communicate with the interior of the balloon so that the working fluid received at the port: i) is first directed to the cover moving member to operate the cover moving member and thus axially move the cover from the covering position to the retracted position; and ii) is then introduced into the interior of the balloon after the cover is axially moved toward the retracted position to outwardly expand the balloon toward the inflated condition.

8. The stent delivery device according to claim 7, wherein
the shaft comprises a first lumen and a second lumen, the first lumen communicating with the port and the second lumen communicating with the interior of the balloon.

9. The stent delivery device according to claim 7, further comprising:
a cylinder housing the cover moving member, the cover moving member being movable within the cylinder to move the cover between the covering position and the retracted position.

10. The stent delivery device according to claim 9, wherein
the cover moving member is a piston, and
the cover moving member is connected to the cover via a wire.

11. The stent delivery device according to claim 9, wherein
the shaft comprises a first lumen and a second lumen, the first lumen communicating with the port and the second lumen communicating with the interior of the balloon;
the cylinder comprises an inlet port connected to the first lumen and an outlet port connected to the second lumen; and
the piston is movable within the cylinder between an open position that allows the working fluid to flow from the inlet port to the outlet port of the cylinder and a closed position that prevents the working fluid from flowing from the inlet port to the outlet port of the cylinder.

12. The stent delivery device according to claim 7, further comprising:
a stent positioned on the outer surface of the balloon when the balloon is in the deflated position, the inflation of the balloon causing the stent to expand radially outwardly.

* * * * *